United States Patent [19]

Baigas, Jr. et al.

[11] Patent Number: 5,013,309

[45] Date of Patent: May 7, 1991

[54] INCONTINENT PAD WITH HIGH ABSORBENT PACKET

[75] Inventors: Joseph F. Baigas, Jr., Charlotte; John T. Haynes, Jr., Waxhaw, both of N.C.

[73] Assignee: Kem-Wove Incorporated, Charlotte, N.C.

[21] Appl. No.: 342,527

[22] Filed: Apr. 24, 1989

[51] Int. Cl.$^5$ .............................................. A61F 13/15
[52] U.S. Cl. .................................... 604/368; 604/381; 604/385.1
[58] Field of Search ............... 604/358, 364, 365, 367, 604/368, 372, 374–377, 378, 384, 381, 385.1

[56] References Cited

U.S. PATENT DOCUMENTS

| | | |
|---|---|---|
| 3,088,463 | 5/1963 | Harmon . |
| 3,554,788 | 1/1971 | Fechillas ............................ 604/364 |
| 3,616,797 | 11/1971 | Champaigne, Jr. ................ 604/364 |
| 3,888,256 | 6/1975 | Studinger . |
| 3,903,889 | 9/1975 | Torr . |
| 3,971,379 | 7/1976 | Chatterjee . |
| 4,010,752 | 3/1977 | Denny ............................... 604/364 |
| 4,102,340 | 7/1978 | Mesek et al. . |
| 4,105,033 | 8/1978 | Chatterjee et al. . |
| 4,232,674 | 11/1980 | Melican . |
| 4,235,237 | 11/1980 | Mesek et al. . |
| 4,250,172 | 2/1981 | Mutzenberg et al. . |
| 4,282,874 | 8/1981 | Mesek ............................... 604/375 |
| 4,287,251 | 9/1981 | King et al. . |
| 4,289,130 | 9/1981 | Usami et al. ...................... 604/378 |
| 4,318,408 | 3/1982 | Korpman et al. .................. 604/368 |
| 4,327,728 | 5/1982 | Elias . |
| 4,338,371 | 7/1982 | Dawn et al. . |
| 4,360,022 | 11/1982 | Usami et al. ...................... 604/375 |
| 4,381,783 | 5/1983 | Elias ................................. 604/368 |
| 4,411,660 | 10/1983 | Dawn et al. . |
| 4,413,995 | 11/1983 | Korpman . |
| 4,429,001 | 1/1984 | Kolpin et al. . |
| 4,559,050 | 12/1985 | Iskra ................................. 604/368 |
| 4,560,372 | 12/1985 | Pieniak . |
| 4,573,988 | 3/1986 | Pieniak et al. . |
| 4,600,458 | 7/1986 | Kramer et al. .................... 604/388 |
| 4,655,757 | 4/1987 | McFarland et al. . |
| 4,657,538 | 4/1987 | Beebe et al. ...................... 604/381 |
| 4,681,577 | 7/1987 | Stern et al. . |
| 4,685,914 | 8/1987 | Holtman . |
| 4,685,915 | 8/1987 | Hasse et al. ...................... 604/378 |
| 4,699,823 | 10/1987 | Kellenberger et al. . |
| 4,718,899 | 1/1988 | Itoh et al. ......................... 604/380 |
| 4,861,652 | 8/1989 | Lippert et al. .................... 604/385.1 |
| 4,880,419 | 11/1989 | Ness ................................. 604/368 |
| 4,889,596 | 12/1989 | Schoggen et al. ................ 604/378 |
| 4,916,005 | 4/1990 | Lippert et al. .................... 604/388 |

*Primary Examiner*—Randall L. Green
*Assistant Examiner*—K. Reichle
*Attorney, Agent, or Firm*—Bell, Seltzer, Park & Gibson

[57] ABSTRACT

An incontinent pad has a pervious inner surface layer and impervious outer surface layer with both layers having edge portions connected together to form an envelope thereat. A high absorbent packet is contained within the formed envelope and overlies major areas of the impervious outer layer. A high loft porous webbed section is in intitmate engagement with the high absorbent packet. The high absorbent packet has at least two juxtapositioned nonwoven webs of textile staple fibers with a layer of superabsorbent powder positioned between all of the adjacent webs. The edges of the webs are sealed together to prevent powder migration from the side. Each of the nonwoven webs of the high absorbent packet also includes a binder to impart sufficient strength to the nonwoven webs for facilitating handling and for allowing movement of the fiber under the expanding influence of the superabsorbent powder.

25 Claims, 2 Drawing Sheets

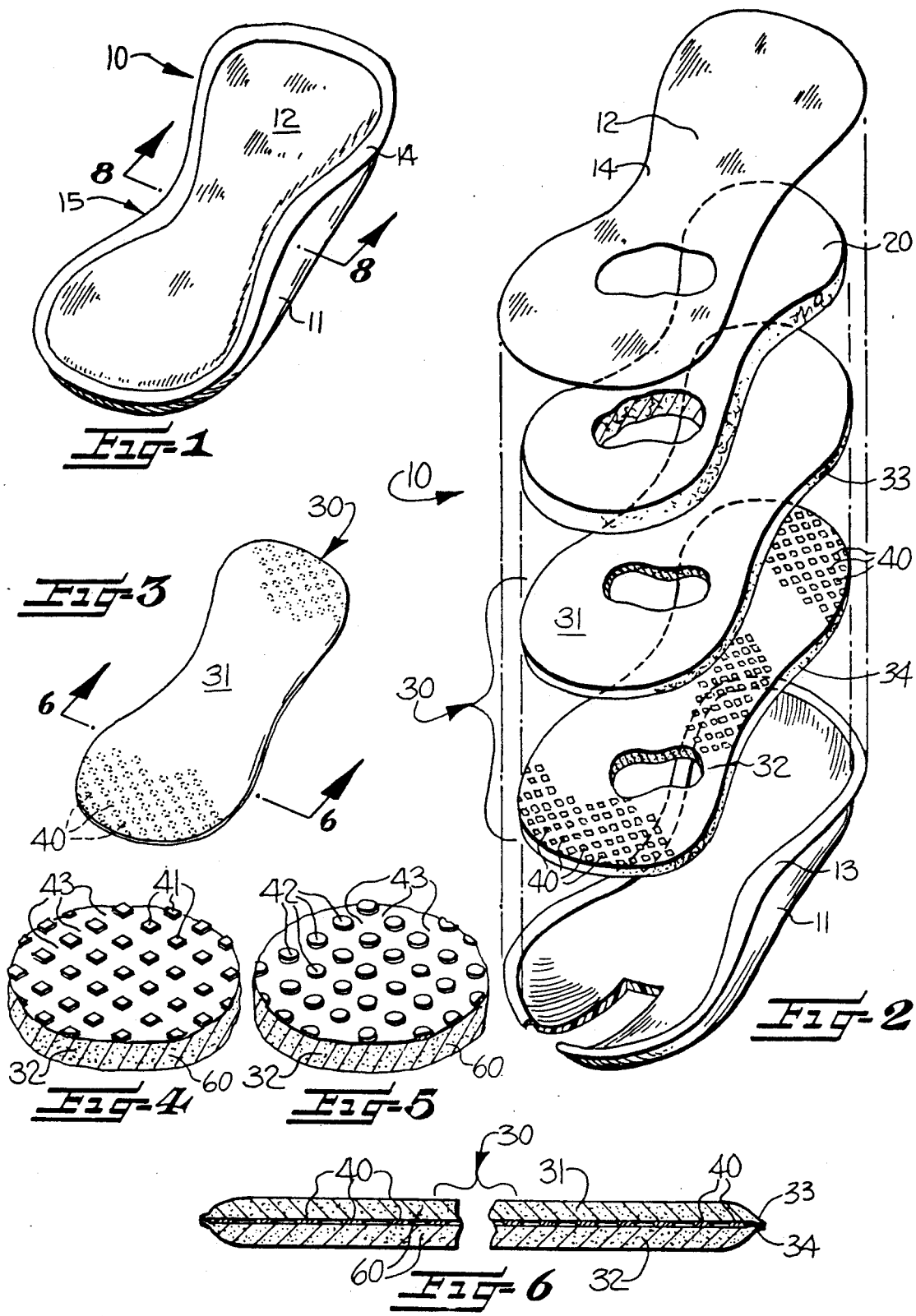

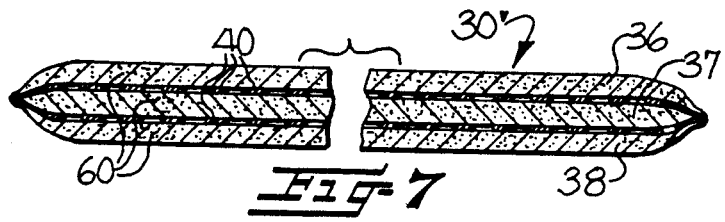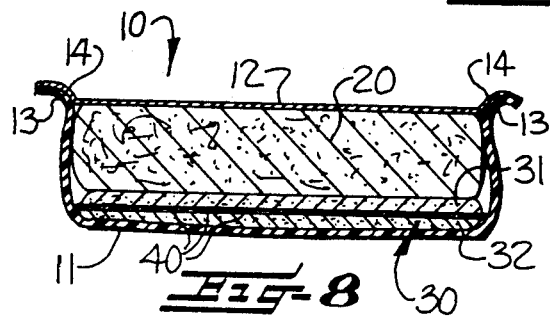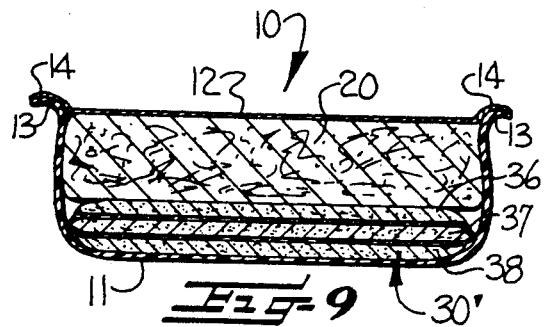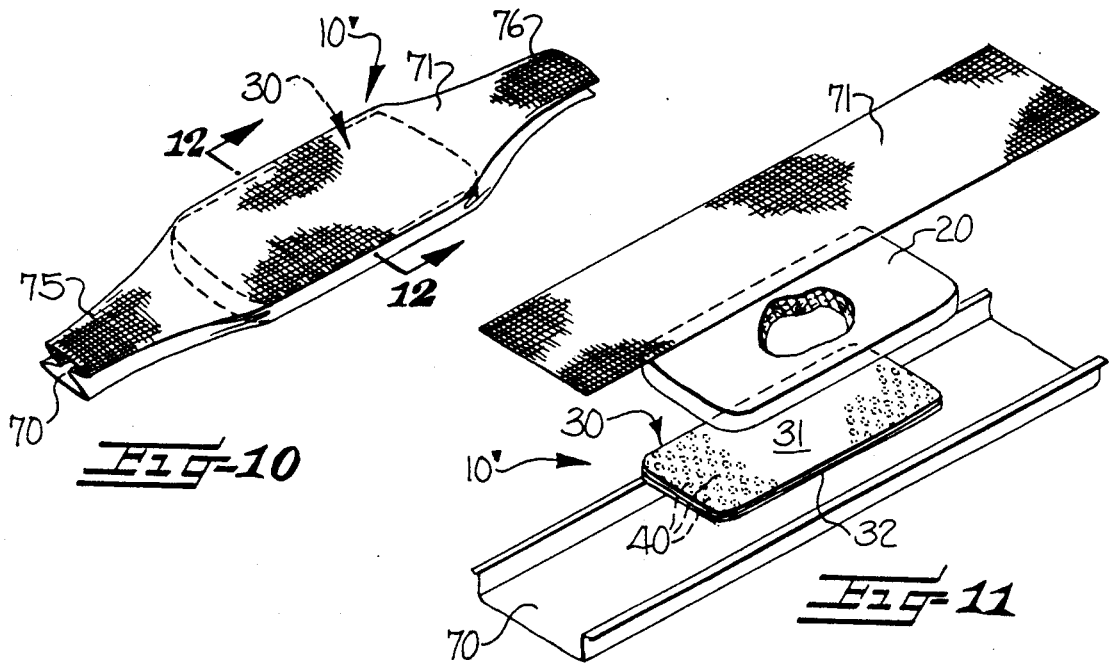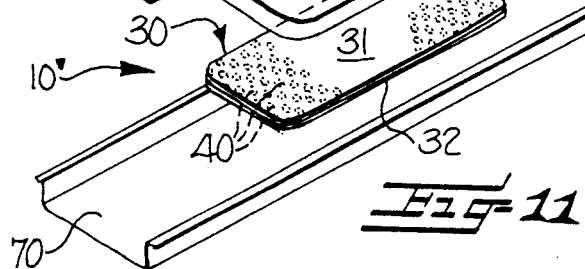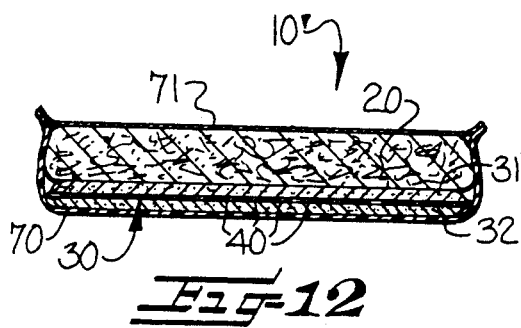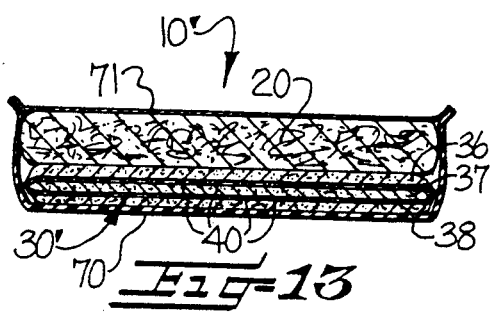

5,013,309

INCONTINENT PAD WITH HIGH ABSORBENT PACKET

FIELD OF THE INVENTION

This invention relates to an incontinent pad having a high absorbent packet inserted therein and more particularly to an incontinent pad with a high absorbent packet having at least two juxtapositioned nonwoven webs of textile staple fibers with a superabsorbent powder layer applied therebetween.

BACKGROUND OF THE INVENTION

Superabsorbent powders which can absorb many times their weight in liquid often are used in association with incontinent and other absorbent pads such as disposable diapers, bandages and decubitus pads to increase the absorptive capacity of the pads. Typically, these pads have a liquid impervious backing layer and a pervious face layer with an absorbent batt or packet formed from wadding, wood pulp, nonwoven webs of textile fibers or other absorbent material positioned between the backing and face layers. To increase the absorptive capacity of the packet, superabsorbent powder is either interspersed throughout the packet or applied to the packet as a superposed layer thereon. When the packet is wetted, the superabsorbent powder absorbs and retains the liquid.

In the past, many applications of superabsorbent powders in incontinent and other absorbent pads were uneconomical. Superabsorbent powders typically are expensive and their application in an absorbent pad mandate the full efficient use and availability of all the superabsorbent powder so that most of the superabsorbent powder is placed in contact with the liquid being absorbed. Unless the absorptive pad provides sufficient room for expansion or gelling of the powder, the powder is limited in the amount of liquid it can absorb and retain since the powder must have room to expand to absorb liquid.

Many prior pads using superabsorbent powder were limited since liquid flowing through the pad encountered a quantity of powder which expanded, gelled and blocked further fluid flow throughout the pad. Some pads were designed in an attempt to minimize the expanding powder blockage by applying the powder to a corrugated fibrous web such as disclosed in U.S. Pat. No. 4,685,914 to Holtman or by providing for an absorbent packet having capillary flow along webs of textile staple fibers which includes deposits of superabsorbent powder applied thereon such as disclosed in U.S. Pat. No. 4,232,674 to Melican.

However, even with improved pad designs, typically powder migration negates any minimization of powder blockage brought about by the improved designs. For example, in pads having respective liquid impervious and pervious back and face layers, powder migrating from convoluted webs or from absorbent packets often collects between the impervious backing layer and the convoluted webs or absorbent packet contained in the pad. Deposits of migrated powder absorb and retain liquid, expanding and gelling to block further fluid flow between the backing layer and the convoluted webs or absorbent packet. In addition, these pads often suffer other drawbacks. Typically, large grained superabsorbent powder particles are used to prevent vertical powder migration through any webs of textile or other staple fibers. Although a fine grained superabsorbent powder particle would provide a higher surface area per weight of powder, thus increasing the efficiency with which a pad can absorb and retain liquid, many commercially available pads are produced from webs having a web porosity which does not prevent fine grained superabsorbent powder from migrating therethrough.

It is therefore an object of this invention to provide an incontinent pad with an absorbent packet having superabsorbent powder contained therein wherein migration of said superabsorbent powder throughout the pad is limited.

It is another object of this invention to provide an incontinent pad with an absorbent packet having superabsorbent powder contained therein, wherein fluid flow through said pad and packet is not restricted by expanding superabsorbent powder.

It is another object of this invention to provide a high absorbent packet which can be positioned between the liquid impervious outer surface and a liquid pervious inner surface of an incontinent pad.

It is another object of this invention to provide a high absorbent packet having a superabsorbent powder contained therein wherein vertical and horizontal migration of the powder through the packet is limited or prevented.

SUMMARY OF THE INVENTION

These and other objects and advantages of the present invention are accomplished by an incontinent pad having a liquid impervious layer adapted to serve as the outer surface of the pad. A nonwoven textile staple fiber face layer defines the inner surface of the pad. The liquid impervious layer and the textile staple fiber face layer each includes edge portions with the edge portions of both layers connected together to form an envelope thereat having a pervious inner surface and impervious outer surface. A high absorbent packet is contained within the formed envelope and overlies major areas of the impervious outer layer. A high loft porous webbed section substantially fills the envelope with one surface of the porous section being in intimate engagement with the high absorbent packet and the opposing surface adapted to be in intimate engagement with the inner face layer when said pad is in use.

The high absorbent packet comprises at least two juxtapositioned nonwoven webs of textile staple fibers. A layer of superabsorbent non-thermoplastic polymer powder is positioned between all of said adjacent layers of the nonwoven webs of textile staple fibers. The average size of the superabsorbent powder particles are between 40 and 150 microns in diameter. The nonwoven webs have such weight, staple length, and denier size of textile staple fibers forming the web so as to prevent superabsorbent powder particularly the smaller particle sizes from migrating through the juxtapositioned webs. The edges of the webs have edge portions sealed together to prevent escape of the superabsorbent powder from within. Each of the nonwoven webs of textile staple fibers also includes a binder thereon to impart sufficient strength to the nonwoven web for facilitating the handling thereof. In the first preferred embodiment, the binder is a water-soluble binder and is positioned on the innermost surfaces of said nonwoven webs.

In the preferred embodiment, the textile staple fibers forming each web within the high absorbent packet have a denier of about 1 to 5 and the weight of each nonwoven web of textile staple fibers within the high absorbent packet is about 1.0 to 3 ounces per square yard. The weight of superabsorbent powder applied between the adjacent layers of the nonwoven webs of textile staple fibers is about 0.095 to 0.60 grams per square inch. The staple length of the fibers in the high absorbent packet is about 0.5 to 3.0 inches.

DETAILED DESCRIPTION OF THE DRAWINGS

Some of the objects and advantages of the present invention having been stated, others will be more fully understood from the detailed description which follows and by reference to the accompanying drawings in which:

FIG. 1 is an isometric view of the incontinent pad in accordance with a first and preferred embodiment of the invention.

FIG. 2 is an exploded isometric view of the first embodiment of the incontinent pad of the present invention showing the high loft porous webbed section and a first embodiment of the high absorbent packet.

FIG. 3 is an isometric view of the high absorbent packet showing the general configuration of the first embodiment of the packet.

FIG. 4 is an isometric view of a nonwoven web in accordance with the present invention showing superabsorbent powder applied to the web in a first discrete pattern motif.

FIG. 5 is an isometric view of a nonwoven web in accordance with the present invention showing superabsorbent powder applied to the web in a second discrete pattern motif.

FIG. 6 is a sectional view taken along line 6—6 of FIG. 3 showing a first embodiment of the high absorbent packet in accordance with the present invention.

FIG. 7 is a sectional view of a second embodiment of the high absorbent packet in accordance with the present invention.

FIG. 8 is a sectional view of the preferred, first embodiment of the incontinent pad taken along line 8—8 of FIG. 1 showing the high absorbent packet in accordance with the first embodiment contained therein.

FIG. 9 is a sectional view of the second embodiment of the incontinent pad showing the high absorbent packet in accordance with the second embodiment contained therein.

FIG. 10 is an isometric view of the incontinent pad in accordance with a second embodiment of the present invention.

FIG. 11 is an exploded isometric view of the second embodiment of the incontinent pad of the present invention showing the relative positioning of the high loft porous webbed section and the high absorbent packet.

FIG. 12 is a sectional view of the first embodiment of the incontinent pad taken along line 12—12 of FIG. 10 showing the high absorbent packet in accordance with the first embodiment contained therein.

FIG. 13 is a sectional view of the second embodiment of the incontinent pad showing the high absorbent packet in accordance with the second embodiment contained therein.

DETAILED DESCRIPTION

Referring to the drawings, and more particularly to FIG. 1, an incontinent pad 10 according to a preferred first embodiment of the invention is shown. The pad 10 includes a liquid impervious layer or shell 11, which serves as the outer surface of the pad, and a nonwoven textile staple fiber face layer 12 defining the inner surface of the pad. Both layers 11, 12 include respective edge portions 13, 14 connected together to form an envelope 15 thereat (FIGS. 8 and 9). A high loft porous webbed section 20 is contained within the formed envelope together with a high absorbent packet 30 (FIGS. 2, 3, 8, 9, 12 and 13). As will be explained in detail later, the high absorbent packet 30 includes at least two juxtapositioned nonwoven webs 31, 32 of textile staple fibers with a layer of superabsorbent non-thermoplastic polymer powder 40 positioned between all of the adjacent layers of the nonwoven webs 31, 32.

The respective edge portions 33, 34 of the webs 31, 32 are sealed together so as to form the high absorbent packet 30. In the illustrated embodiments, the respective edge portions 33, 34 are substantially co-extensive and have peripheral edge portions sealed together. Each of the nonwoven webs 31, 32 also includes a binder 60 thereon to impart sufficient strength to the nonwoven webs for facilitating handling and allowing movement of the textile fibers under the expanding influence of the superabsorbent powder 40 when it is wetted (FIGS. 6 and 7).

Referring now more particularly to FIG. 2, there is shown in detail the liquid impervious layer or shell 11, the fiber face layer 12, the high loft porous webbed section 20 and an exploded view of the nonwoven webs 31, 32 forming the high absorbent packet 30. As illustrated, the liquid impervious layer or shell 11 is shaped in a conventional manner similar to some commercially available female incontinence devices, i.e. concave with a more narrow medial portion. Other shapes, e.g. rectangular, also can be used.

The shell 11 can be formed from a molded foam by conventional thermal molding processes. Typically, the shell is about 0.06"-0.25" thick with a formed depth of around 0.5" to 2.5". Although the size and shape of the shell 11 can vary, typically, the length of the shell ranges from about 4" to about 12", with a width from about 2" to 7". The shell 11 acts as a protective barrier against wetness seeping from the packet 30. The high loft porous webbed section 20 and high absorbent packet 30 are contained within the interior of the shell 11 and are retained therein by the fiber face layer 12, which, as noted before has its edge portions 14 sealed to the edge or rim 13 of the shell 11 by means conventional in the art so as to provide a unitary product. Although the nonwoven textile staple fiber face layer 12 is formed of a nonwoven construction of polyester staple fibers, the face layer can be woven as long as sufficient porosity is maintained. Other staple fiber materials can be substituted as long as the fiber face layer retains sufficient strength and porosity to allow liquid flow therethrough.

The high absorbent packet 30 is contained within the liquid impervious shell 11 and overlies major areas of the shell 11. As illustrated, the high absorbent packet 30 is geometrically shaped to conform to the shape of the outer shell 11. However, close shape conformity of the packet 30 to the outer shell 11 is not necessary as long as the packet substantially overlies major areas of the liquid impervious shell to provide a substantially absorbent section within the shell and resultant formed pad 10. A rectangularly shaped high absorbent packet 30 could be used since the medial portion of the packet could be compressed to fit within the more narrow medial portion of the shell 11.

The high loft porous webbed section 20 overlies the high absorbent packet 30 and substantially fills the envelope 15 formed by the interconnected liquid impervious shell 11 and the fiber face layer 12. Preferably, the porous webbed section 20 is formed from polyester staple fibers processed by conventional means into a high loft web. When the webbed section 20 is inserted into the formed envelope 15 between respective shell and face layers 11, 12, the section not only imparts loft to the structure of the pad 10, but allows substantial memory or recoverability to the pad so that when the pad is compressed, folded or twisted, the pad may recover to its original shape and volume after the deforming pressure is released. Although the illustrated embodiment shows the porous webbed section 20 cut into a shape substantially conforming to the shape of the concave liquid impervious shell 11, a substantially rectangular shaped section 20 also can be used since portions of the high loft webbed section 20 can be compressed to enable the section to conform to the shape of the shell 11 and fit therein.

As illustrated, the porous webbed section 20 is retained within the pad 10 by the fiber face layer 12. When the incontinent pad 10 is in use, the porous webbed section 20 not only allows fluid to pass therethrough to the high absorbent packet 30, but in addition, the porous webbed section 20 aids in maintaining the structural integrity of the pad 10 during use. As will be explained in detail hereafter, liquid reaching the high absorbent packet 30 is absorbed by the superabsorbent powder 40 contained therein. Since the high loft porous webbed section 20 is readily compressible, any pressure exerted by the liquid saturated and now enlarged high absorbent packet will not adversely affect the structural integrity of the pad 10.

Referring now more particularly to FIGS. 10 through 13, a second embodiment of the incontinent pad 10' in accordance with the present invention is illustrated wherein the liquid impervious layer is formed from a relatively thin plastic sheet 70. Additionally, the thin plastic sheet 70 can be laminated to a soft nonwoven fabric so as to impart resilience and strength thereto. Enclosed within the envelope formed by the thin plastic sheet 70 and nonwoven staple textile fiber face layer 71 are the high loft porous webbed section 20 and the high absorbent packet 30. As illustrated, the pad 10' includes terminal end portions which are sealed so as to form elongate, flattened strips 75, 76 at either end of the pad 10'. The end strips 75, 76 facilitate handling and use of the incontinent pad 10' since the strips can include tie strings or adhesive tape (not shown) for maintaining the pad in a desired placed relation on an individual's body. To prevent the face layer 71 from disconnecting with the plastic sheet 70, conventional sealing means such as an adhesive is utilized at terminal end portions forming the strips 75, 76 as well as at medial portions thereof.

The particular advantage of this second embodiment of the incontinent pad 10' is the lowered manufacturing cost relative to the first and preferred embodiment of the incontinent pad 10 formed from a thermal processed preformed foam, liquid impervious shell 11 with a fiber face layer 12 connected thereto. The production of the liquid impervious shell 11 adds to the overall cost of the pad 10. Although the second embodiment does not include a more thick, liquid impervious shell 11 to act as a barrier against wetness, in many applications, the plastic sheet material is a sufficient barrier minimizing leakage of fluid from the pad 10'.

Referring now to FIGS. 3, 6 and 7, the high absorbent packet 3 in accordance with the present invention comprises at least two juxtapositioned nonwoven webs 31, 32 of textile staple fibers having a layer of superabsorbent powder 40 applied between all of the adjacent layers of the nonwoven webs. As illustrated, the peripheral edge portions 33, 34 of the webs are substantially co-extensive and have peripheral edge portions sealed together to prevent escape of the superabsorbent powder 40 positioned between all of the adjacent web layers. The respective edge portions 33, 34 are substantially co-extensive and have peripheral edge portions sealed together Each of the nonwoven webs 31, 32 includes a water soluble binder 60 to impart sufficient strength to the nonwoven webs for facilitating handling thereof. When the webs are wetted, the water soluble binder 60 dissolves allowing movement of the fibers of the webs 31, 32 under the expanding influence of the superabsorbent powder 40 which inherently expands as it absorbs water, thus facilitating flow within the absorbent packet 30.

Preferably, the nonwoven webs 31, 32 of textile staple fibers are formed from polyester staple fibers having a staple length of between 0.5" to 3.0" and preferably around 1.5". Longer staple length fibers are undesirable since the longer staple length fibers are more difficult to process and any formed nonwoven webs are less apt to have adequate uniformity throughout the web. The polyester staple fibers are advantageous since they provide a strong web structure. Even when wetted, the webs 31, 32 maintain their structure.

To provide greater efficiency of the superabsorbent powder 40, the superabsorbent powder particles are more fine than those particles typically utilized in many commercially available incontinent devices. Finer superabsorbent powder particles provide greater surface area contact of the particles with liquid flowing through the high absorbent packet 30. In accordance with the present invention, the average size of the superabsorbent powder particles are between about 40 and 150 microns and preferably average about 90 microns in diameter. In addition, the shorter staple length of the fibers, i.e. under 3" is necessary to minimize the number of large voids in the webs 31, 32. Large voids are undesirable since they allow superabsorbent powder to migrate therethrough. Normally, this fine a superabsorbent powder would migrate through many nonwoven webs provided in many commercially available incontinent and other absorbent devices. In fact, most commercially available incontinent pads include a superabsorbent powder applied between webs where the average size of the superabsorbent powder particles is about 175 microns. However, it has been determined that migration of fine superabsorbent particles having an average size of between 40 to 150 microns is minimized by forming each web 31, 32 to have such weight, staple length, and denier size of textile staple fibers forming the web so as to prevent superabsorbent powder, particularly the smaller particle sizes, from migrating through the juxtapositioned nonwoven webs.

Conventional carding and other processing means are utilized to manufacture each web 31, 32 from polyester textile staple fibers having an approximate 1-5 denier and a staple length of between 0.5" and 3.0", and preferably, the webs are manufactured to a web weight of approximately 1.0 to 3 ounces per square yard. This processing within these parameters has been found sufficient to limit Frazier permeability test equipment to a value ready of less than 244 feet per minute air flow at a 0.5 inch water gauge pressure drop so as to prevent migration of superabsorbent particles having an average particle size as fine as 40 microns.

Commercially available brands of superabsorbent powder which have been found successful with the present invention include all commercially available brands such as polyacrylic acid and polyacrylic amid, potassium based hydrolyzed starch and sodium polyacrylate. These powders can absorb up to ninety times their weight in one percent saline solution. One percent saline solution is isotropic with body fluids. In distilled water this ratio might be as high as 800 to 1. The amounts deposited between adjacent webs can be small compared with the actual amount of water which the formed high absorbent packet 30 will absorb. As will be explained in detail later, depending on the number of nonwoven webs used with the packet 30, approximately 0.095 to 0.6 grams per square inch of superabsorbent powder 40 can be applied between adjacent layers of nonwoven webs 31, 32.

Some of the particular advantages of the present invention are not only the nonwoven webs 31, 32 having a porosity such that superabsorbent powder 40 having an average particle size as fine grained as 40 microns will not migrate therethrough, but also the lack of fluid access blockage caused by expanding and gelling superabsorbent powder. This latter advantage is accomplished by the unique application of finite amounts of superabsorbent powder 40 between all of the adjacent nonwoven webs 31, 32 and the application of a water soluble binder 60, which upon contact with a liquid, is dissolved to allow expansion of the nonwoven webs and provide substantially unrestricted open areas of fluid flow throughout the packet 30 even as the superabsorbent powder expands. This especially is advantageous with the present invention where fine superabsorbent powder particles are utilized. Finer superabsorbent particles increase the overall surface area of contact between the superabsorbent powder particles and fluid flowing through the packet 30. Thus, fluid is absorbed faster by those particles which first come in contact with the powder, thus increasing the speed of inherent powder expansion. In many conventional designs, the rapidly expanding superabsorbent powder effectively would limit further fluid flow since the expanded powder would block fluid travel past the now expanded powder. As noted before, the present invention minimizes this problem by providing open areas of flow throughout the high absorbent packet 30.

It has been determined that open areas of the flow in the high absorbent packet 30 can be provided by the use of the water soluble binder 60 for allowing movement of the web under the expanding influence of the superabsorbent powder 40, and either the application of superabsorbent powder between adjacent layers of nonwoven webs in a discrete pattern motif or the use of more than three nonwoven web layers with reduced powder application between all of the adjacent webs so as to provide open channels of flow within the nonwoven webs. For example, referring to FIGS. 4 and 5 there are shown two respective examples of superabsorbent powder 40 applied in a pattern, i.e. respective square and circular patches 41, 42. In a first embodiment of the high absorbent packet as shown in FIG. 6, the superabsorbent powder 40 is applied in a pattern, square or circular, between the two nonwoven webs 31, 32. Preferably each web 31, 32 is approximately one and a half ounces per square yard. Approximately 0.2 grams per square inch of powder 40 is applied in a pattern as disclosed. Although the combination of weights is preferred, other web and powder weights are not restricted as long as the Frazier permeability test equipment reading is maintained under 244.

The patterned arrangement provides fluid channels 43 between individual patches of powder through which fluid may travel. As the high absorbent packet 30 is wetted, the water soluble binder 60 dissolves while simultaneously any superabsorbent powder expands as it is contacted by the liquid absorbed into the packet. Even though the superabsorbent powder expands, enough open channel space 43 is retained between powder patches 41, 42 to allow liquid flow therethrough. The powder 40 also may expand against the nonwoven webs 31 32 since the water soluble binder 60 has dissolved allowing movement of the fiber outward to account for the expanding influence of the powder.

Referring now to FIG. 7, a second embodiment of the high absorbent packet 30' is illustrated where three nonwoven webs of textile staple fibers 36, 37, 38 are used and a layer of superabsorbent powder is applied between all of the adjacent webs. Preferably, the webs 36, 37, 38 are 1.25 ounces per square yard. This thickness of a web is substantially thinner than corresponding webs 31, 32 of the first embodiment where only two nonwoven webs were used. The thinness of the webs is at times necessary to minimize the increased thickness of the high absorbent packet 30' created by the use of three webs instead of two webs. The amount of powder 40 applied between each of the adjacent webs also is reduced as compared to the embodiment having two webs 31, 32 and as little as 0.095 grams per square inch of powder are applied. The packet 30 having three web layers 36, 37, 38 and a smaller amount of powder 40 between each of the adjacent webs will retain the same amount of absorptive capacity as the preferred first embodiment of the packet 30.

Although the illustrated embodiment shows the powder 40 applied in patches between the adjacent webs 36, 37 and 38, this second embodiment of the high absorbent packet 30' is advantageous since the superabsorbent powder does not have to be applied in a patterned arrangement as shown in FIGS. 5 and 6 to provide open areas for liquid flow. Thus, the complexity of applying superabsorbent powder in a patterned arrangement is avoided. The three layers of nonwoven webs 36, 37, 38 actually can provide the open areas for fluid flow. The forces exerted by the expanding superabsorbent powder 40 against the nonwoven webs 36, 37, 38 are spread over three nonwoven webs instead of two webs 31, 32 as in the first embodiment (FIG. 6). The increased web area and reduced forces generated on each web 36, 37, 38 allow each nonwoven web to in effect become an open channel for fluid flow therethrough. As noted before, the powder 40 also may be applied in patterns between the three nonwoven web layers 36, 37, 38 providing additional open channel flow around the patches therein. In the illustrated embodiments only two distinct patter motifs were illustrated, i.e. circular or square patches. Other pattern motifs are equally usable and could include such patterns as diamond patches, a spiral design or other convoluted designs which provide open flow channels.

As noted before, a binder 60 is applied to each nonwoven web by conventional means during manufacture of the web such as a spray application. The binder 60 should provide sufficient bonding strength to the fibers forming the nonwoven web to impart sufficient strength for facilitating handling thereof The amount of binder applied to each web can vary depending on the type and properties of the binder. However, typically the amount of binder applied is approximately ten percent of the weight of the web. In the preferred embodiment, the binder 60 is water soluble and positioned on the innermost surfaces of the nonwoven webs of the packet 30 for allowing movement of the nonwoven webs under the expanding influence of the superabsorbent powder 40 when the superabsorbent powder is wetted and inherently expanding so as to facilitate flow within the absorbent packet. One water soluble binder 60 now commercially available which has been found suitable for use in accordance with the present invention is polyvinyl alcohol.

Additionally, a binder 60, formed from fibrillated fibers, is positioned on the outer surfaces of the nonwoven webs of the packet 30 and causes water received thereon to be spread over a wide area of the webs so as to obtain contact with a wider area of the superabsorbent powder. The fibrillated fibers are of a length of 20 to 200 microns and a width from 0.5 microns to 5 microns. These fibrillated fibers can be suspended in water in weight (water/fiber) percentages up to 4% and spray applied to a non-woven web by normal spray techniques. When water is evaporated by drying, the fibrillated structure formed thereat ties the fibers of the nonwoven web at crossing points by entanglement. The fibrillated fibers attain their strength and ability to cling together by hydrogen bonding. Preferably, the fibrillated fibers are formed from cellulose acetate.

The high absorbent packets 30, 30' are manufactured by means conventional in the art. The nonwoven webs are manufactured by conventional air lay or carding, although air lay is preferred since isotropic strength characteristics are improved. Each manufactured web is then bonded by conventional means such as air spraying the polyvinyl acetate on each carded or air laid web after formation. The required number of webs, i.e, two or three, then are assembled together with powder spreaders applying the superabsorbent powder either evenly therebetween or in timed sequence to produce the desired discrete pattern motif. The formed composite structure is simultaneously die cut and sealed under high heat and pressure in accordance with known techniques to produce the high absorbent packet having its edge portions sealed together to prevent escapement of the superabsorbent powder from within. The high heat and pressure is necessary to provide the necessary seal since the superabsorbent powder is not thermoplastic, even at high temperatures.

The foregoing embodiments are to be considered illustrative rather than restrictive of the present invention and those modifications which come within the meaning and range of equivalents of the claims are to be included therein.

That which is claimed is:

1. An incontinent pad comprising a liquid impervious layer defining the outer surface of the pad, a nonwoven staple fiber face layer defining the inner surface of the pad, and wherein said liquid impervious layer and said textile staple fiber face layer each includes edge portions with the edge portions of both layers connected together to form an envelope thereat having a pervious inner surface and impervious outer surface, a high absorbent packet contained within said formed envelope and overlying major areas of the impervious outer layer, and a high loft porous webbed section substantially filling the envelope with one surface of the porous section being in intimate engagement with said high absorbent packet and the opposing surface of the face layer, said high absorbent packet comprising at least two juxtapositioned nonwoven webs of textile staple fibers, a layer of superabsorbent non-thermoplastic polymer powder positioned between all of said adjacent layers of said nonwoven webs of textile staple fibers and wherein the average size of the superabsorbent powder particles are between 40 and 150 microns in diameter, and said nonwoven webs have a weight of 1.0 to 3 ounces per square yard, and are formed of staple fibers having a length of between 0.5" to 3.0" and a denier of about 1 to 5 so as to provide a Frazier permeability test equipment value reading of less than 244 feet per minute air flow at a 0.5 inch water gauge pressure drop so as to prevent superabsorbent powder, particularly the smaller particle sizes, from migrating through the juxtapositioned nonwoven webs, said webs having edge portions sealed together to prevent escapement of the superabsorbent powder from within, and each of said nonwoven webs of textile staple fibers having binder means thereon to impart sufficient strength to the nonwoven web for facilitating the handling thereof.

2. The incontinent pad according to claim 1 wherein said binder means is a water soluble binder and is positioned on the innermost surfaces of said nonwoven webs for allowing movement of the fiber of said nonwoven webs under the expanding influence of the superabsorbent powder when the superabsorbent powder is wetted and inherently expanding so as to facilitate flow within the absorbent packet.

3. The incontinent pad according to claim 2 wherein said water soluble binder means is polyvinyl alcohol.

4. The incontinent pad according to claim 1 wherein said binder means is on the outer surfaces of said nonwoven webs, and said binder means being formed from fibrillated fibers and causing water received thereon to be spread over a wide area of the webs for thus obtaining contact with a wider area of said superabsorbent powder.

5. The incontinent pad according to claim 1 wherein said impervious outer surface is formed from a relatively thin plastic sheet material impervious to the passage of liquids and air therethrough.

6. The incontinent pad according to claim 1 wherein the superabsorbent powder between all of said adjacent layers of said nonwoven webs of textile staple fibers is in a discrete pattern motif.

7. The incontinent pad according to claim 1 wherein the high absorbent packet includes more than two nonwoven webs of textile staple fibers.

8. The incontinent pad according to claim 6 wherein the superabsorbent powder is positioned between all of said adjacent layers of the nonwoven webs of textile staple fibers in substantially uniform distribution.

9. The incontinent pad according to claim 6 wherein the superabsorbent powder is positioned between at least two adjacent layers of the nonwoven webs of textile staple fibers in a discrete pattern motif.

10. The incontinent pad according to claim 1 wherein said binder means on each nonwoven web of textile staple fiber is about 10% of the weight of the web.

11. The incontinent pad according to claim 1 wherein the weight of the superabsorbent powder applied between adjacent layers of said nonwoven webs of textile staple fibers is about 0.095 to 0.6 grams per square inch.

12. The incontinent pad according to claim 1 wherein the average size of the superabsorbent powder particles are about 90 microns.

13. The high absorbent packet according to claim 1 wherein said binder means is a water soluble binder and is positioned on the innermost surfaces of said nonwoven webs for allowing movement of the fiber of said nonwoven webs under the expanding influence of the superabsorbent powder when the superabsorbent powder is wetted and inherently expanding so as to facilitate flow within the absorbent packet.

14. The incontinent pad according to claim 1 wherein said binder means is on the outer surfaces of said nonwoven webs, and said binder means being formed from fibrillated fibers and causing water received thereon to be spread over a wide area of the webs for thus obtaining contact with a wider area of said superabsorbent powder.

15. An incontinent pad comprising a liquid impervious layer defining the outer surface of the pad, a nonwoven textile staple fiber face layer defining the inner surface of the pad, and wherein said liquid impervious layer and said textile staple fiber layer each includes edge portions with the edge portions of both layers connected together to form an envelope thereat having a pervious inner surface and impervious outer surface, a high absorbent packet contained within said formed envelope and overlying major areas of the impervious outer layer, and a high loft porous webbed section substantially filling the envelope with one surface of the porous section being in intimate engagement with said high absorbent packet and the opposing surface of the face layer, said high absorbent packet comprising at least two juxtapositioned nonwoven webs of textile staple fibers, a layer of superabsorbent non-thermoplastic polymer powder positioned between all of said adjacent layers of said nonwoven webs of textile staple fibers and wherein the average size of the superabsorbent powder particles are between 40 to 150 microns in diameter, and wherein said textile staple fibers forming said nonwoven webs have a staple length of between 0.5" to 0.3" a denier of about 1.5 and the weight of each nonwoven web of textile staple fibers is about 1.0 to 3 ounces per square yard so as to provide a Frazier permeability test equipment value reading of less than 244 feet per minute air flow at a 0.5 inch water gauge pressure drop so that the textile staple fibers forming the web prevent superabsorbent powder, particularly the smaller particle sizes, from migrating through the juxtapositioned webs, said webs having edge portions sealed together to prevent escapement of the superabsorbent powder from within, and each of said nonwoven webs of textile fibers having binder means thereon to impart sufficient strength to the nonwoven web for facilitating the handling thereof.

16. A high absorbent packet comprising at least two juxtapositioned nonwoven webs of textile staple fibers, a layer of superabsorbent non-thermoplastic polymer powder positioned between all of said adjacent layers of said nonwoven webs of textile staple fibers and wherein the average size of the superabsorbent powder particles are between 40 and 150 microns in diameter and said nonwoven webs have a weight of 1.0 to 3 ounces per square yard, and are formed of staple fibers having a length of between 0.5" to 3.0" and a denier of about 1 to 5 so as to provide a Frazier permeability test equipment value reading of less than 244 feet per minute air flow at 0.5 inch water gauge pressure drop so as to prevent superabsorbent powder, particularly the smaller particle sizes, from migrating through the smaller particle sizes, from migrating through the juxtapositioned nonwoven webs, said webs having edge portions sealed together to prevent escapement of the superabsorbent powder from within, and each of said nonwoven webs of textile staple fibers having binder means thereon to impart sufficient strength to the nonwoven web for facilitating the handling thereof.

17. The high absorbent packet according to claim 16 wherein the superabsorbent powder between all of said adjacent layers of said nonwoven webs of textile staple fibers is in a discrete pattern motif.

18. The high absorbent packet according to claim 16 wherein the packet includes more than two nonwoven webs of textile staple fibers.

19. The high absorbent packet according to claim 18 wherein the superabsorbent powder is positioned between all of said adjacent layers of the nonwoven webs of textile staple fibers in substantially uniform distribution.

20. The high absorbent packet according to claim 18 wherein the superabsorbent powder is positioned between at least two adjacent layers of the nonwoven webs of textile staple fibers in a discrete pattern motif.

21. The high absorbent packet according to claim 16 wherein said binder means on each nonwoven web of textile staple fibers is about 10% of the weight of a web.

22. The high absorbent packet according to claim 16 wherein the weight of the superabsorbent powder applied between the adjacent layers of said nonwoven webs of textile staple fibers is about 0.095 to 0.6 grams per square inch.

23. The high absorbent packet according to claim 16 wherein the average size of the superabsorbent powder particles is about 90 microns.

24. The high absorbent packet according to claim 16 wherein said superabsorbent powder is selected from the group consisting of polyacrylic acid and polyacrylic amid, a potassium based hydrolyzed starch, and sodium polyacrylate.

25. The high absorbent packet according to claim 17 wherein said water soluble binder means is polyvinyl alcohol.

* * * * *